(12) United States Patent
Williams

(10) Patent No.: US 10,639,078 B2
(45) Date of Patent: May 5, 2020

(54) SPINAL IMPLANT SYSTEM AND METHOD

(71) Applicant: Warsaw Orthopedic, Inc, Warsaw, IN (US)

(72) Inventor: Seth K. Williams, Madison, WI (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 103 days.

(21) Appl. No.: 15/353,626

(22) Filed: Nov. 16, 2016

(65) Prior Publication Data
US 2017/0135728 A1 May 18, 2017

Related U.S. Application Data

(60) Provisional application No. 62/256,280, filed on Nov. 17, 2015.

(51) Int. Cl.
*A61B 17/70* (2006.01)

(52) U.S. Cl.
CPC ........ *A61B 17/705* (2013.01); *A61B 17/7002* (2013.01); *A61B 17/7032* (2013.01)

(58) Field of Classification Search
USPC .................................................. 606/259–260
See application file for complete search history.

(56) References Cited

U.S. PATENT DOCUMENTS

| | | | | |
|---|---|---|---|---|
| 6,004,349 A * | 12/1999 | Jackson | ............. | A61B 17/7032 411/3 |
| 6,102,912 A * | 8/2000 | Cazin | ................. | A61B 17/7004 606/259 |
| 7,329,258 B2 * | 2/2008 | Studer | ................ | A61B 17/7028 606/250 |
| 8,425,556 B2 * | 4/2013 | Le Roux | ............ | A61B 17/7007 606/246 |
| 9,089,369 B2 * | 7/2015 | Biedermann | ........ | A61B 17/705 |
| 9,283,003 B2 * | 3/2016 | Iott | ..................... | A61B 17/7002 |
| 9,301,784 B2 * | 4/2016 | Zhao | ..................... | A61B 17/705 |
| 10,105,163 B2 * | 10/2018 | Keyer | .................... | A61B 17/705 |
| 2005/0065514 A1 * | 3/2005 | Studer | ................ | A61B 17/7028 188/379 |
| 2005/0277932 A1 * | 12/2005 | Farris | .................. | A61B 17/7014 606/260 |
| 2006/0129147 A1 * | 6/2006 | Biedermann | ...... | A61B 17/7004 128/897 |
| 2006/0212033 A1 * | 9/2006 | Rothman | ............ | A61B 17/7028 606/328 |
| 2006/0229611 A1 * | 10/2006 | Avery | ................. | A61B 17/7011 606/260 |
| 2006/0282080 A1 * | 12/2006 | Albert | ................ | A61B 17/7011 606/247 |
| 2008/0045951 A1 * | 2/2008 | Fanger | ............... | A61B 17/7005 606/86 A |

(Continued)

*Primary Examiner* — Jan Christopher L Merene

(57) ABSTRACT

A spinal construct includes an existing spinal rod implant defining a rod dimension and having at least one mating surface. At least one extension includes a mating surface engageable with the at least one mating surface of the existing spinal rod implant to comprise a connection having a dimension the same as the rod dimension. A coupling member is configured to fix the existing spinal rod implant with the at least one extension. Systems, surgical instruments, implants and methods are disclosed.

18 Claims, 8 Drawing Sheets

(56) References Cited

U.S. PATENT DOCUMENTS

| | | | | |
|---|---|---|---|---|
| 2008/0177388 A1* | 7/2008 | Patterson | ........... | A61B 17/7031 623/17.16 |
| 2008/0215095 A1* | 9/2008 | Biedermann | ...... | A61B 17/7031 606/246 |
| 2009/0171395 A1* | 7/2009 | Jeon | ................... | A61B 17/7007 606/257 |
| 2009/0177232 A1* | 7/2009 | Kiester | ................ | A61B 17/705 606/260 |
| 2009/0204153 A1* | 8/2009 | Suzuki | ................. | A61B 17/705 606/250 |
| 2010/0049252 A1* | 2/2010 | Smisson, III | ...... | A61B 17/7043 606/250 |
| 2010/0114167 A1* | 5/2010 | Wilcox | ............. | A61B 17/7004 606/250 |
| 2012/0310285 A1* | 12/2012 | Zhao | ................... | A61B 17/705 606/264 |

\* cited by examiner

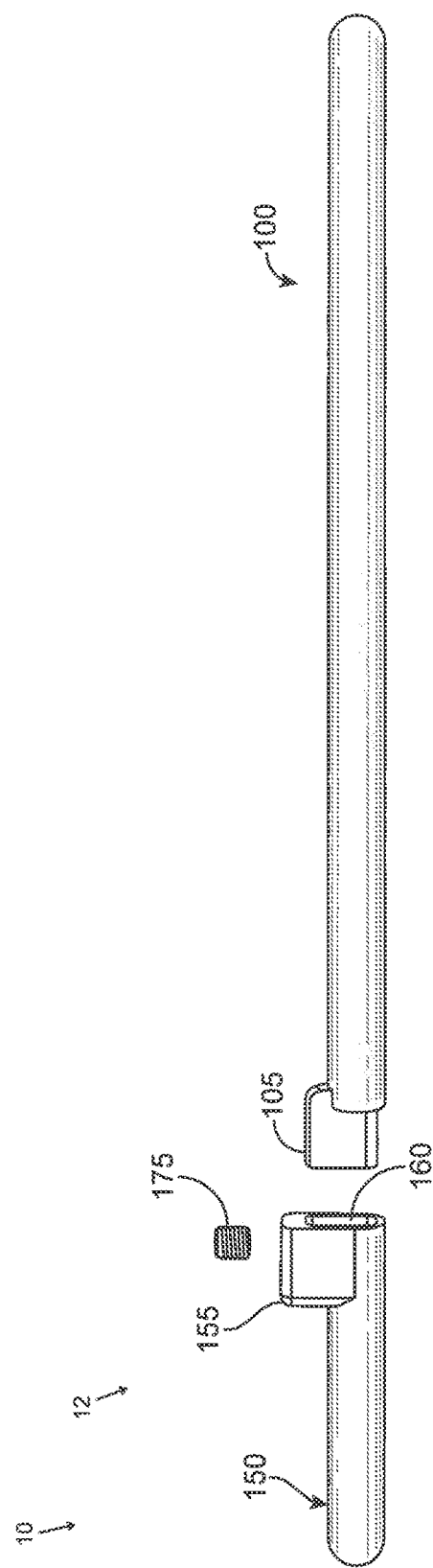
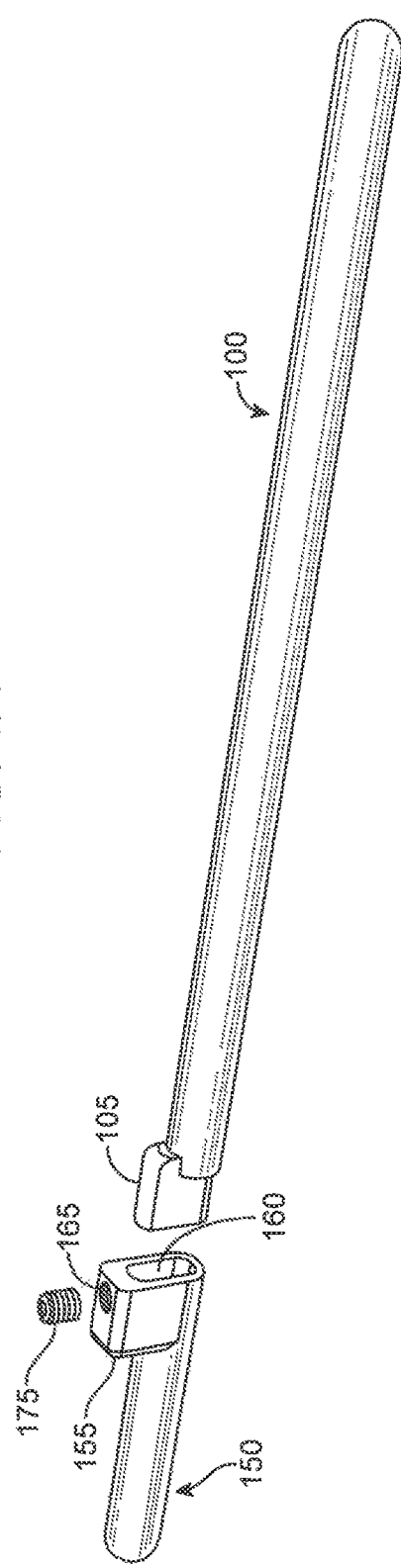

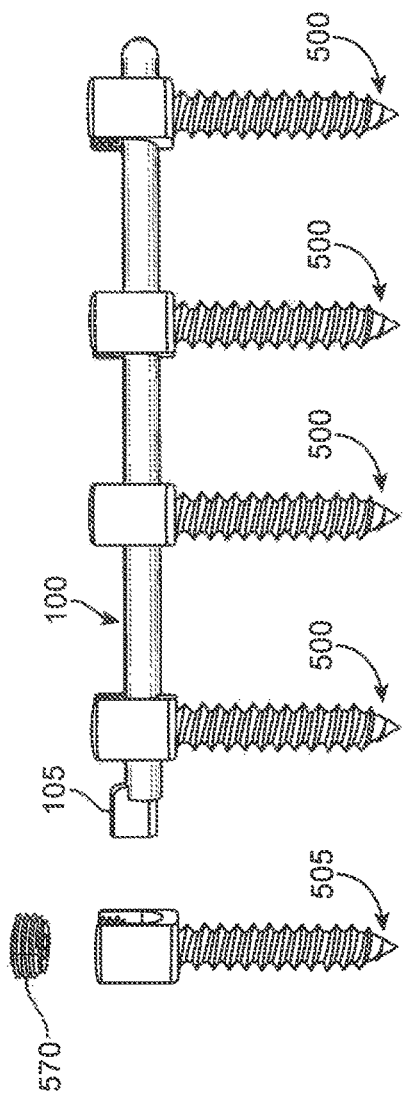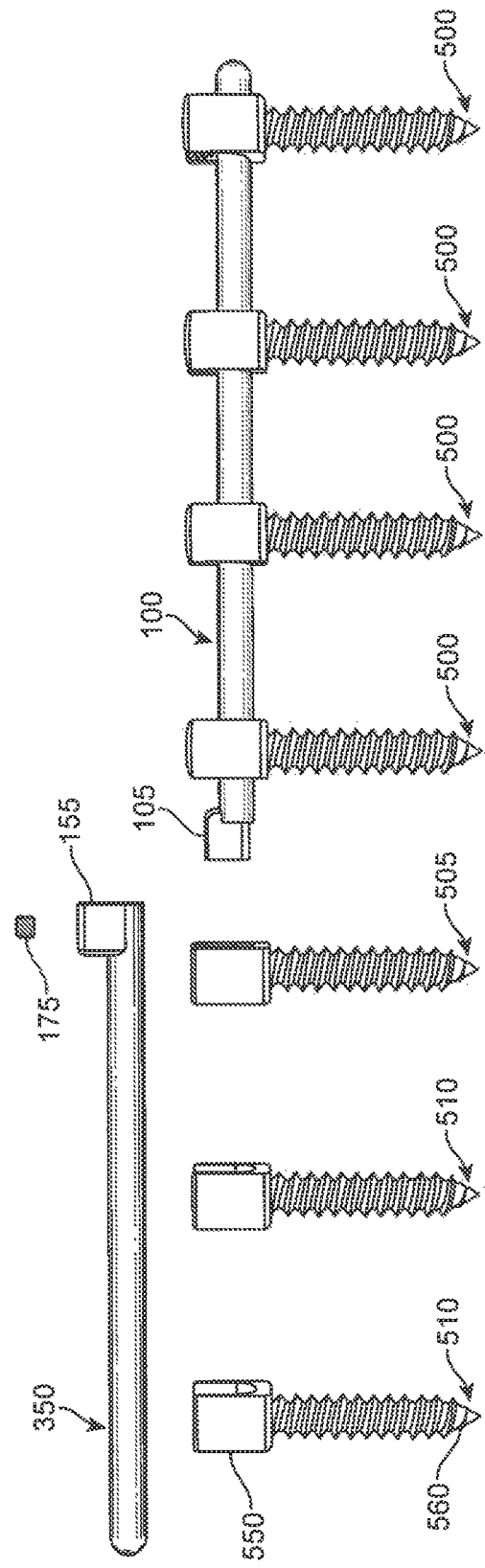

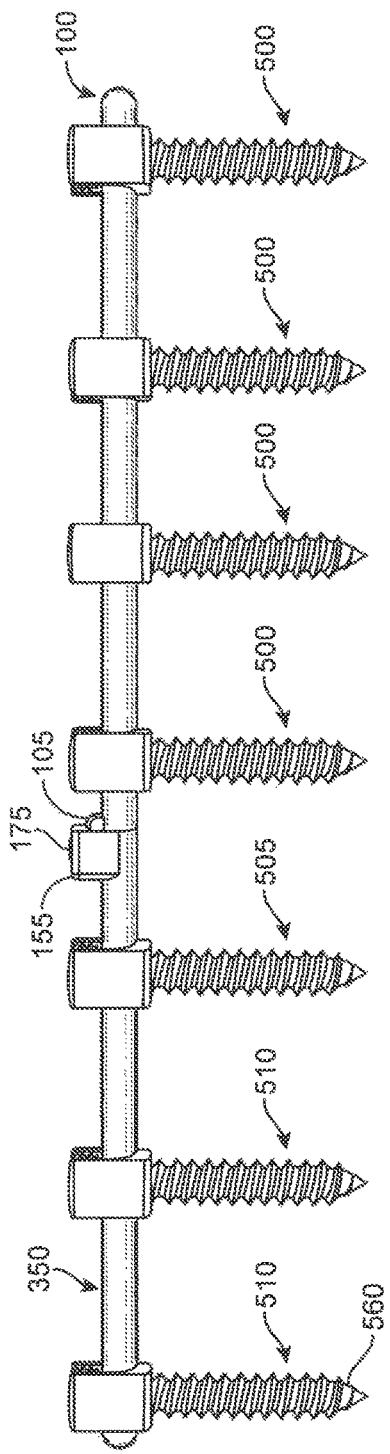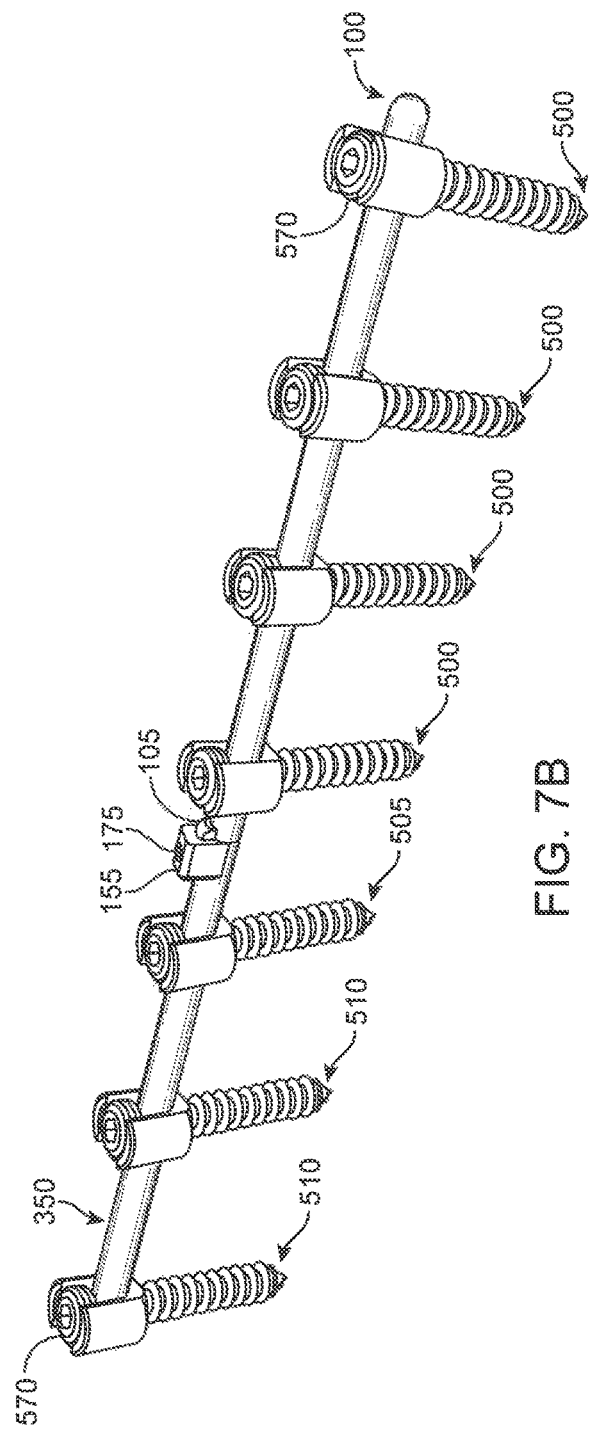
FIG. 7A
FIG. 7B

SPINAL IMPLANT SYSTEM AND METHOD

CROSS REFERENCE TO RELATED APPLICATION

This application claims the benefit of the filing date of U.S. Provisional Application No. 62/256,280, filed on Nov. 17, 2015, the contents of which being hereby incorporated by reference herein in its entirety.

TECHNICAL HELD

The present disclosure generally relates to medical devices for the treatment of musculoskeletal disorders, and more particularly to a spinal implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a spinal construct is provided. The spinal construct includes an existing spinal rod implant defining a rod dimension and having at least one mating surface. At least one extension includes a mating surface engageable with the at least one mating surface of the existing spinal rod implant to comprise a connection having a dimension the same as the rod dimension. A coupling member is configured to fix the existing spinal rod implant with the at least one extension. In some embodiments, systems, surgical instruments, implants and methods are disclosed.

In one embodiment, a preemptive spinal rod system is provided. The preemptive spinal rod system includes a rod portion and a rod extension portion or portions. The rod extension portion includes a connector end that is configured to mate with an end of the rod portion such that a medial-to-lateral diameter of a connection region between the rod portion and the rod extension portion is the same as a diameter of the rod portion. A fastener is configured to secure the rod extension portion to the rod portion.

BRIEF DESCRIPTION OF THE DRAWINGS

The present disclosure will become more readily apparent from the specific description accompanied by the following drawings, in which:

FIG. 1A is a perspective view of components of one embodiment of a system in accordance with the principles of the present disclosure;

FIG. 1B is a perspective view of the components shown in FIG. 1A;

FIG. 6A is a side view of components of one embodiment of a system in accordance with the principles of the present disclosure;

FIG. 6B is a side view of components of one embodiment of a system in accordance with the principles of the present disclosure;

FIG. 7A is a side view of components of one embodiment of a system in accordance with the principles of the present disclosure;

FIG. 7B is a perspective view of the components shown in FIG. 7A; and

DETAILED DESCRIPTION

Figure 2A:
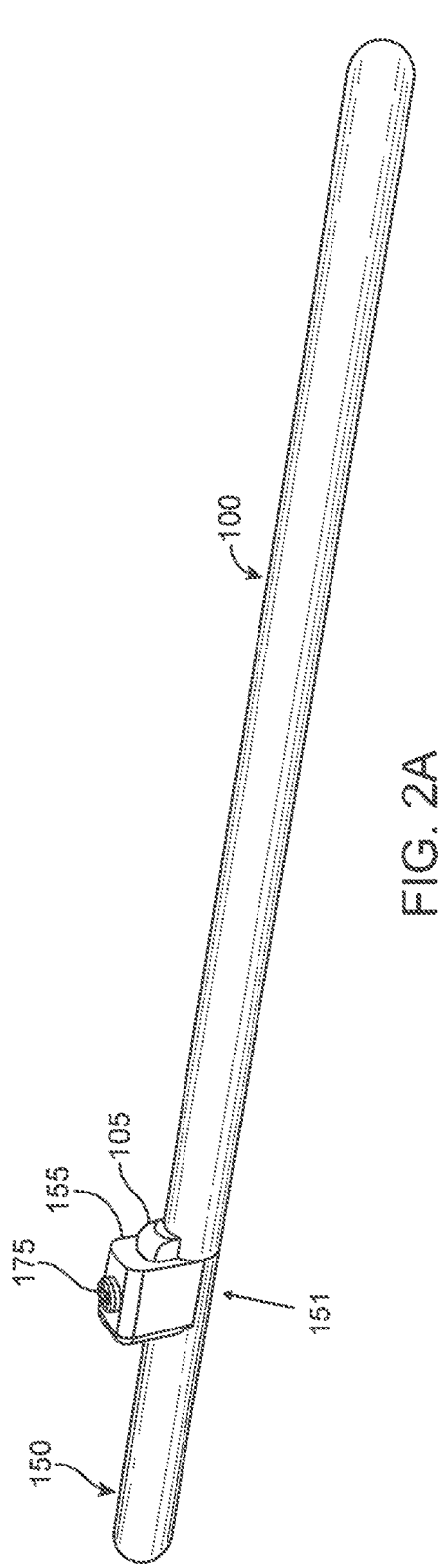
FIG. 2A is a perspective of components of one embodiment of a system in accordance with the principles of the present disclosure.

The exemplary embodiments of the surgical system and related methods of use disclosed are discussed in terms of medical devices for the treatment of musculoskeletal disorders and more particularly, in terms of a surgical system and method for treatment of a spine disorder. In some embodiments, the systems and methods of the present disclosure are employed with a spinal joint fusion, for example, with a cervical, thoracic, lumbar and/or sacral region of a spine.

In some embodiments, the present system comprises a spinal construct that includes an existing spinal rod implant engageable with at least one extension to comprise a connection having a dimension uniform with a dimension of the existing spinal rod implant. In some embodiments, the configuration of the spinal construct avoids adding bulk to the spinal rod, for example, in a revision surgery and can be disposed with existing fastener implants and/or newly implanted fasteners. In some embodiments, the present system includes a preemptive spinal rod system having a rod portion, a rod extension portion or portions, and a fastener or fasteners. In some embodiments, the rod extension portion includes a connector end that is configured to mate with an end of the rod portion such that a medial-to-lateral diameter of a connection point between the rod portion and the rod extension portion is the same as a diameter of the rod portion. In some embodiments, the fastener is configured to secure the rod extension portion to the rod portion.

In some embodiments, the present system includes a spinal rod that can accommodate a single spinal rod extension. In some embodiments, the present system is employed with a method of securing the spinal rod to a spinal rod extension. In some embodiments, the present system is employed with a method of assembling a spinal rod and a spinal rod extension to comprise a preemptive spinal rod system that is used in an index or initial spine surgery. In some embodiments, the spinal rod is secured to an elongated spinal rod extension. In some embodiments, the present system includes a spinal rod that can accommodate two spinal rod extensions. In some embodiments, the spinal rod is secured to two spinal rod extensions and comprise a preemptive spinal rod system. In some embodiments, the present system is employed with a method of securing a first spinal rod extension to a spinal rod, with the spinal rod and the first spinal rod extension secured to pedicle screws. In some embodiments, the method includes the step of securing the second spinal rod extension to the spinal rod, with the spinal rod and the second spinal rod extension secured to pedicle screws.

In some embodiments, the present system includes spinal instrumentation to stabilize a spine for a spinal fusion. In some embodiments, the spinal instrumentation can include a spinal rod, which is secured to one or more vertebrae via pedicle screws. In some embodiments, the present system is employed with a method to treat adjacent segment deterioration, which can occur above or below an instrumented spinal fusion. In some embodiments, the method can include revision surgery and/or an overall longer spinal rod.

In some embodiments, the present system includes a spinal rod system having a modular spinal rod with spinal segments that are mounted to one another in a way that does not significantly increase the overall bulk of the spinal rod. In some embodiments, the modular spinal rod can be employed with a revision surgery that occurs after the modular spinal rod is in place and/or implanted with tissue. In some embodiments, one or more segments of the spinal rod can be replaced by longer segments during the revision surgery, for example, a minimally invasive surgery or conventional open surgery. In some embodiments, during a revision surgery, a first portion and/or a second portion, for example, a top portion and/or bottom portion of an existing spinal rod implant is removed from a main part of the rod, and a rod portion, for example, an extension, which is longer than the first and/or second portions, can be attached to the main part of the rod. In some embodiments, the extension extends the existing spinal rod implant in one or more directions, for example, up or down, into newly placed and/or implanted pedicle screws. In some embodiments, the extension can pass through one or more previously placed pedicle screws and pass through one or more newly placed and/or implanted pedicle screws.

In some embodiments, the present surgical system includes a spinal construct that can be employed with a method for treating a spine with a plurality of spinal rod portions, which can be used to hold a spine until fusion occurs. In some embodiments, the present surgical system includes a spinal construct that can be employed with a method for treating a spine, which includes a pedicle subtraction osteotomy, a transforaminal lumbar interbody fusion (TLIF) and/or long constructs in heavy patients. In some embodiments, the spinal construct includes a spinal rod disposed with a multi-axial (MAS), fixed axis (FAS) or a sagittal adjusting (SAS) pedicle screw.

In some embodiments, the spinal construct includes revision instrumentation configured to attach to one or more existing spinal constructs implanted with a body. In some embodiments, the spinal construct can be employed in a revision surgery to extend an existing screw and rod construct. In some embodiments, the spinal construct can be employed in a revision surgery to connect an existing spinal construct and extend the existing spinal construct to span one or more spinal levels.

In some embodiments, the present surgical system includes a spinal construct that can be employed in a revision surgery to connect to an existing rod implanted with a body. In some embodiments, the spinal construct and the existing spinal construct comprise an extension. In some embodiments, the present surgical system includes a spinal construct that can be employed in a revision surgery to connect to an existing bone screw and rod construct through a minimally invasive approach.

In some embodiments, one or all of the components of the surgical system may be disposable, peel-pack, pre-packed sterile devices. One or all of the components of the system may be reusable. The system may be configured as a kit with multiple sized and configured components.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a spinal construct, related components and methods of employing the surgical system in accordance with the principles of the present disclosure. Alternate embodiments are disclosed. Reference is made to the exemplary embodiments of the present disclosure, which are illustrated in the accompanying figures. Turning to FIGS. 1A and 1B, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a minimally invasive procedure, including percutaneous techniques, mini-open and open surgical techniques to deliver and introduce instrumentation and/or components of spinal constructs at a surgical site within a body of a patient, for example, a section of a spine. In some embodiments, one or more of the components of spinal implant system 10 are configured for engagement with existing constructs, which may include fastener implants and/or spinal rod implants attached with vertebrae, in a revision surgery to manipulate tissue and/or correct a spinal disorder, as described herein. In some embodiments, one or more of the components of spinal implant system 10 can be employed in a revision surgery to connect an existing spinal construct and extend, revise or repair the existing spinal construct to span one or more spinal levels. Spinal implant system 10 comprises a spinal construct 12. In some embodiments, one or more components of spinal construct 12 are configured to extend an existing spinal rod implant with or without removing portions of the existing rod implant. In some embodiments, existing spinal constructs may include one or more implants of spinal implant system 10 connected or fixed with tissue in a prior or different surgical procedure, separate in time and/or over a duration of time in the same surgical procedure.

Spinal construct 12 includes a spinal rod 100 that can accommodate a single spinal rod extension. Spinal rod 100 is connectable with a spinal rod extension 150. Spinal rod 100 and spinal rod extension 150 can be straight as shown, or can be curved to accommodate a patient's anatomy. Spinal rod 100 includes a shaft portion that defines a rod diameter dimension d1 and an end 105. Spinal rod extension 150 includes a shaft portion that defines a rod diameter dimension d2 and an end 155. End 155 defines an opening 160 that is configured to receive end 105 of spinal rod 100.

Figure 2B:
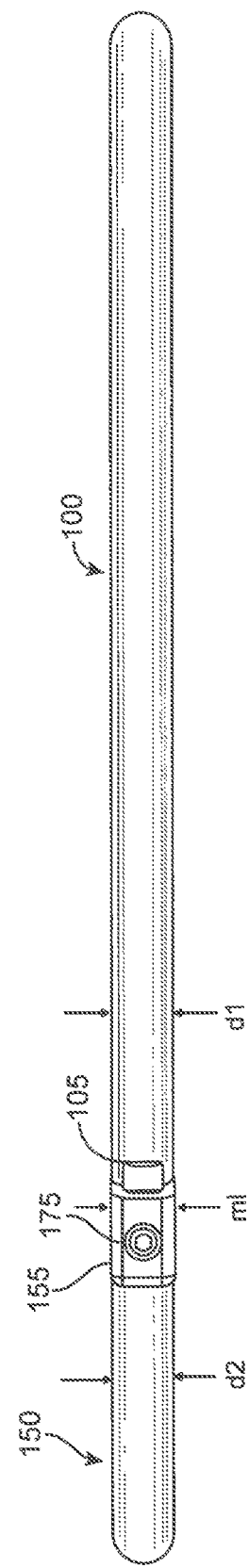
FIG. 2B is a side view of the components shown in FIG. 2A.

Opening 160 is configured such that a male/female connection 151 between spinal rod 100 and spinal rod extension 150 has the same dimension, such as, for example, a medial-to-lateral thickness, diameter or width m1 as rod diameter dimension d1 of spinal rod 100 and/or rod diameter dimension d2 of spinal rod extension 150, as shown in FIGS. 2A and 2B. End 105 includes a male mating part and end 155 includes a female mating part. Connection 151 can freely fit within and/or pass through a U-shaped head of a pedicle screw, as described herein. In some embodiments, connection 151 can pass freely through the pedicle screw head in a cephalad/caudal manner. In some embodiments, this configuration facilitates placement of the components of spinal construct 12, for example, spinal rod 100 and attached spinal rod extension 150, being placed in a percutaneous manner such that the rod portions of a spinal construct pass freely through a pedicle screw head and any pedicle screw head extensions.

Connection 151 between spinal rod 100 and spinal rod extension 150 is secured by a coupling member, such as, for example, a screw 175. In some embodiments, screw 175 includes a set screw that is configured to pass through and engage a threaded hole 165 in spinal rod extension 150 and contact an outer surface of end 105 of spinal rod 100. As set screw 175 is tightened, it presses against an outer surface of end 105 and secures spinal rod extension 150 to spinal rod 100. In some embodiments, screw 175 extends through a threaded hole in spinal rod extension 150 and through a threaded hole in end 105 of spinal rod 100. In some embodiments, two or more screws 175 may be used to secure connection 151. In some embodiments, connection 151 may include the ends of spinal rod 100 and spinal rod extension 150 disposed in alternate fixation configurations, such as, for example, friction fit, pressure fit, locking protrusion/recess, locking keyway and/or adhesive. In some embodiments, dimensions m1, d1, d2 are equal, substantially the same, the same, constant and/or uniform. In some embodiments, portions of spinal rod 100 and spinal rod extension 150 may include different dimensions. In some embodiments, portions of spinal rod 100 and/or spinal rod extension 150 may include different dimensions than connection 151. In some embodiments, dimension m1, dimension d1 and/or dimension d2 may include length, width, height, thickness, diameter, circumference, area and/or volume.

Figure 3A:
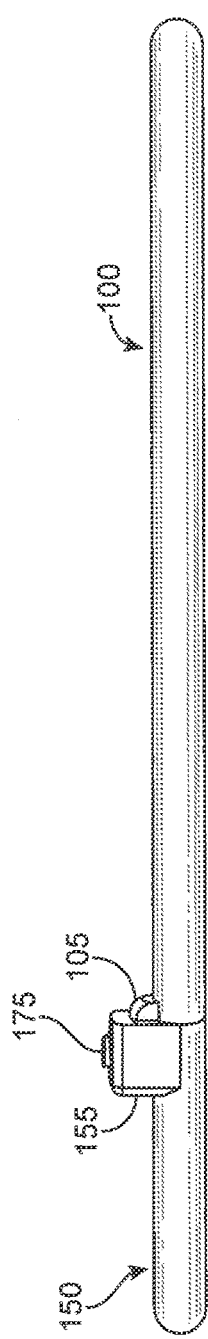
FIG. 3A is a side view of the components shown in FIG. 2A.

In some embodiments, spinal rod extension 150 is secured to spinal rod 100 to comprise components of spinal implant system 10 including a preemptive spinal rod system, similar to the systems described herein, which is used in an index or initial spine surgery, as shown in FIGS. 2A, 2B and 3A. In use, spinal rod extension 150 includes end 155 with opening 160 (FIGS. 1A and 1B), which receives end 105 of spinal rod 100 and is secured by screw 175 to comprise connection 151. Set screw 175 is configured to pass through and engage a threaded hole in spinal rod extension 150 and make contact with an outer surface of end 105 of spinal rod 100. As set screw 175 is tightened, it presses against an outer surface of end 105 and secures spinal rod extension 150 to spinal rod 100. Spinal rod extension 150 is connected, attached, provisionally fixed, permanently fixed and/or secured to spinal rod 100.

As shown in FIG. 2B, spinal rod extension 150 is secured to spinal rod 100 showing that medial-to-lateral dimension m1 of spinal rod extension end 155 and its attachment site to spinal rod end 105 is the same as rod diameter dimension d2 of spinal rod extension 150 and rod diameter dimension d1 of spinal rod 100. This configuration enables connection 151 to fit within a U-shaped head of a pedicle screw, such that it can pass freely through the pedicle screw head in a cephalad/caudal manner. Medial-to-lateral dimension m1 is consistent and/or uniform throughout the rod-to-rod connection. In some embodiments, connection 151 is configured to fit within a rigid U-shaped head of a pedicle screw. In some embodiments, connection 151 comprises a connection region that is the same width as rod diameter dimensions d1, d2. In some embodiments, connection 151 is larger end/or taller in a sagittal plane of a body than rod diameter dimensions d1, d2 to have a connection of sufficient strength to withstand expected loads. In some embodiments, to accommodate a variety of biomechanical stresses at connection 151 and/or between spinal rod 100 and spinal rod extension 150, spinal rod extension end 155 and spinal rod end 105 may be configured with wider medial-to-lateral diameters, which may strengthen connection 151. In some embodiments, connection 151 may be configured with wider medial-to-lateral diameters and prevented from passing through selected pedicle screw heads.

Figure 3B:
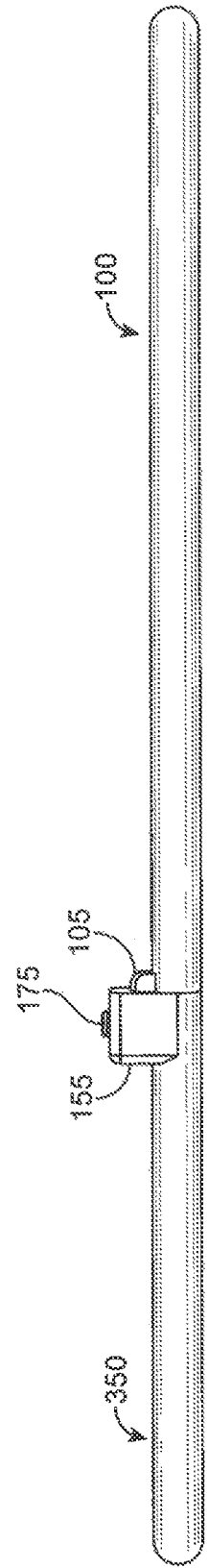
FIG. 3B is a side view of components of one embodiment of a system in accordance with the principles of the present disclosure.

In one embodiment, as shown in FIG. 3B, a spinal construct, similar to spinal construct 12 described herein, includes an elongated spinal rod extension 350 that is secured to spinal rod 100 to comprise components of a spinal rod system, similar to the systems described herein. Spinal rod extension 350, similar to extension 150 described herein, includes an end 155 with an opening 160. A connection, similar to connection 151 described herein, between spinal rod 100 and spinal rod extension 350 is secured by screw 175, described herein, which passes through and engages a threaded portion of end 155 and presses tightly against an outer surface of end 105 of spinal rod 100. As such, the spinal construct can include a spinal rod extension configured in a variety of lengths. In some embodiments, spinal rod 100 can be configured in a variety of lengths. In some embodiments, spinal rod 100 and/or spinal rod extension 150, 350 can be configured with various bends to accommodate a patient's anatomy.

Figure 4A:
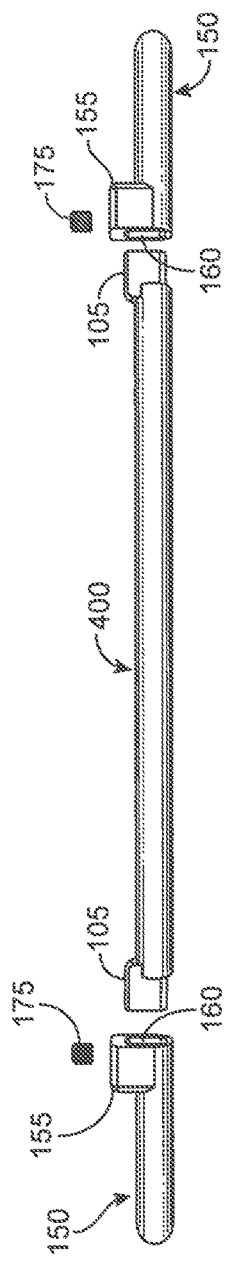
FIG. 4A is a perspective view of components of one embodiment of a system in accordance with the principles of the present disclosure.
Figure 4B:
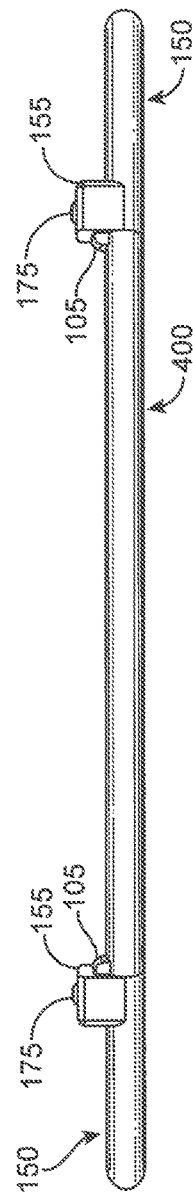
FIG. 4B is a &de view of the components shown in FIG. 4A.
Figure 4C:
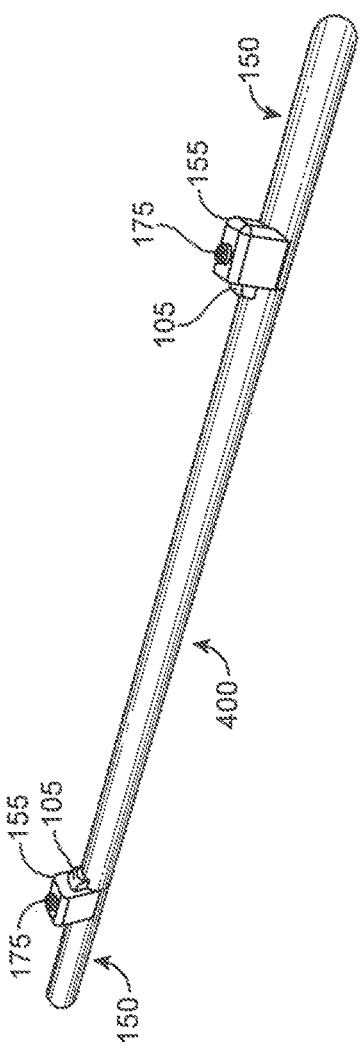
FIG. 4C is a perspective view of the components shown in FIG. 4B.

In one embodiment, as shown in FIGS. 4A, 4B and 4C, a spinal construct, similar to spinal construct 12 described herein, includes a double-ended spinal rod 400 that is configured with two ends 105. Each end 105 can be attached to a spinal rod extension 150. One spinal rod extension 150 is disposed at each end of spinal rod 400, similar to that described herein. Spinal rod extension 150 includes an end 155 with an opening 160 that is configured to receive an end 105 of spinal rod 400. Connections, similar to connection 151 described herein, between spinal rod 400 and spinal rod extensions 150 are secured by screws 175, similar to that described herein.

In some embodiments, two spinal rod extensions 150 are attached to each end of spinal rod 400 to comprise components of a preemptive spinal rod system, similar to the systems described herein, which is used in an index or initial spine surgery, as shown in FIGS. 4B and 4C. For example, the spinal construct, as shown in FIGS. 4B and 4C, can be employed with a clinical use for a preemptive spinal rod system, as described herein. In some embodiments, the spinal construct, as described herein, may be employed with a method for treating a spine that includes shortening the spinal construct in a second or revision surgery. For example, the spinal construct is implanted in an index surgery that involves fusing across one or two intervertebral levels. In some cases, for example, due to biomechanical concerns of instrumenting only the fused levels, the spinal construct is extended beyond the fused levels into unfused spinal segments. The spinal construct is implanted with tissue during the index surgery such that during revision surgery after the fusion has healed, the rod extension(s), as described herein, which extend into unfused spinal segments can be removed, leaving in place the spinal rod, as described herein, which spans only the fused segments. In some embodiments, this configuration of the preemptive spinal rod system allows for shortening of the spinal construct without disturbing the spinal rod and screws that span the fused segment. In some embodiments, a spinal construct, similar to those described herein, may be employed with a method for treating a spine that includes lengthening an instrumentation construct in a revision surgery.

Figure 5A:
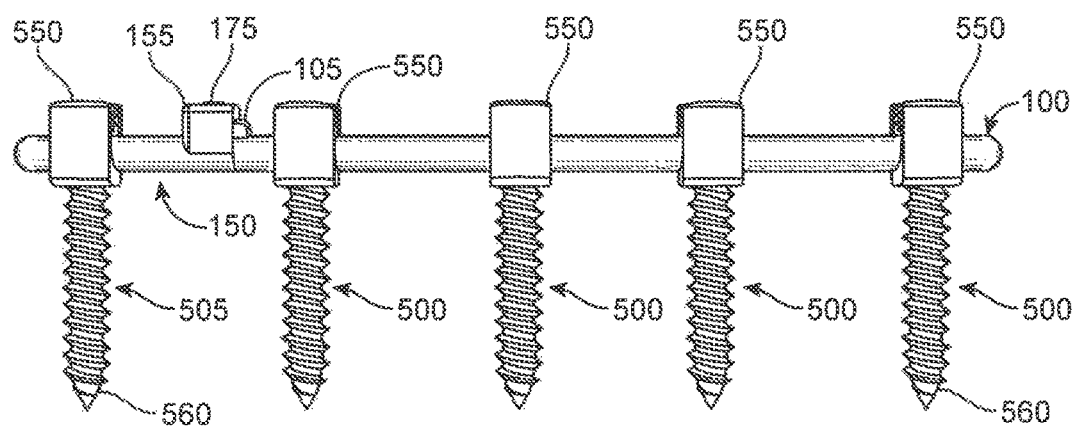
FIG. 5A is a side view of components of one embodiment of a system in accordance with the principles of the present disclosure.
Figure 5B:
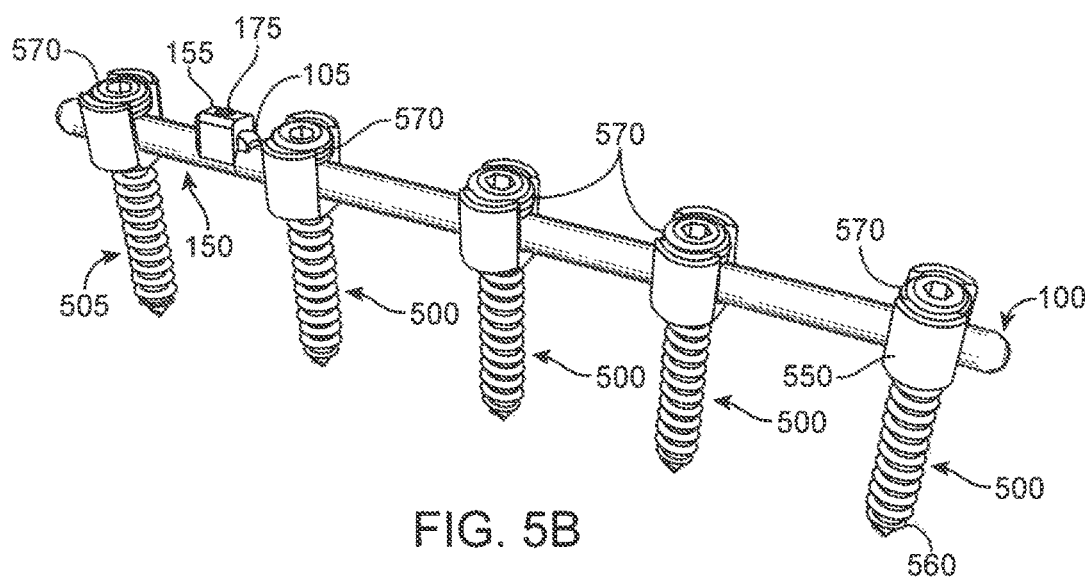
FIG. 5B is a perspective view of the components shown in FIG. 5A.

In one embodiment, as shown in FIGS. 5A and 5B, a spinal construct, similar to spinal construct 12 described herein, may be employed with a method for treating a spine, similar to that described herein. The spinal construct includes spinal rod extension 150 secured to spinal rod 100, as described with regard to FIGS. 2A, 2B, and 3A. Spinal rod extension 150 and spinal rod 100 are secured to pedicle screws 500 and 505. Connection 151 between end 105 of spinal rod 100 and end 155 of spinal rod extension 150 is secured by screw 175. Pedicle screws 500 and 505 are generally of the same design and configured to be interchangeable. Pedicle screws 500 are secured to spinal rod 100 and pedicle screw 505 is secured to a spinal rod extension 150. Pedicle screws 500 and 505 each comprise a threaded shaft 560 and a screw head 550. Set screws 570 pass through and engage a threaded portion of pedicle screw head 550 and press tightly against an outer surface of a spinal rod, similar to those described herein to secure the spinal rod to the pedicle screws.

Spinal rod extension 150 is attached to spinal rod 100. Spinal rod extension 150 and spinal rod 100 are attached to pedicle screws 500 and 505, for example, which would be used in an initial or index surgery. In some embodiments, each of pedicle screws 500 and 505 are secured to a patient and inserted into sequential vertebra, thus spanning five vertebral bodies (not shown) and four disk levels (not shown) to be fused. Spinal rod 100 is secured to a patient via three pedicle screws 500, and rod extension 150 is secured to the patient by a single pedicle screw 505. In some embodiments, one or more additional spinal rod extensions may be used during the initial or index spinal surgery. In some embodiments, the spinal construct, as shown in FIGS. 5A and 5B, may be revised in a surgical procedure to extend the existing spinal construct across more vertebra. For example, the revision procedure can be performed by removing the first spinal rod extension 150 and replacing it with a longer spinal rod extension, as described herein, which attaches to newly placed and/or implanted additional pedicle screws, as described herein, for example, with regard to FIGS. 6A, 6B, 7A and 7B.

In one embodiment, as shown in FIGS. 6A, 6B, 7A and 7B, a spinal construct, similar to spinal construct 12 described herein, may be employed with a method for treating a spine, similar to that described herein. Set screw 570 is removed from pedicle screw 505 and screw 175 is removed from a first and/or existing spinal rod extension 150 to disengage first spinal rod extension 150 from both spinal rod 100 and pedicle screw 505. First spinal rod extension 150 is removed from the patient entirely. The existing spinal construct, as shown in FIG. 6A, shows first spinal rod extension 150 having been removed in a revision surgery and spinal rod 100 secured to pedicle screws 500. Pedicle screw 505 has not been removed from the patient during revision surgery and remains in place to secure a newly placed, elongated spinal rod extension 350, as shown in FIG. 6B. In some embodiments, an insertion tool may be attached to end portion 105 to facilitate percutaneous placement of second rod extension 350. New pedicle screws 510, similar to pedicle screws 500 and 505, have been implanted in a patient to extend the spinal construct across two more vertebra (not shown). Pedicle screws 500 are secured to spinal rod 100 and pedicle screws 505, 510 are secured to second spinal rod extension 350. New pedicle screws 510 will accommodate the longer second rod extension 350. In some embodiments, one or more new pedicle screws 510 can be implanted during a revision surgery, and a second rod extension of variable length placed. In some embodiments, a double-ended spinal rod with spinal rod extensions at both ends, similar to that described with regard to FIGS. 4A, 4B and 4C, can be placed during the index surgery. In some embodiments, one or both of the first spinal rod extensions can be replaced with longer second spinal rod extension(s) that attach to new pedicle screws 510.

Second spinal rod extension 350 is secured to spinal rod 100, and spinal rod 100 and second spinal rod extension 350 are secured to pedicle screws 500, 505, 510, as described herein and shown in FIGS. 7A and 7B. Spinal rod extension 350 is secured to spinal rod 100 to comprise components of a preemptive spinal rod system, similar to the systems described herein, and used in a revision spine surgery, similar to the surgical procedures described herein. The connection, similar to connection 151 described herein, between end 105 of spinal rod 100 and end 155 of second spinal rod extension 350 is secured by screw 175. Set screws 570 secure spinal rod 100 and attached spinal rod extension 350 to pedicle screws 500, 505, 510. Pedicle screws 500, 505 were implanted in the index surgery. During revision surgery, pedicle screw 505 remains in place and set screw 570 is removed to allow for rod removal, as described herein. Pedicle screws 510 are newly implanted during the revision surgery, and may span one or more additional vertebra (not shown). In some embodiments, two new pedicle screws 510 are implanted in two new vertebra (not shown) and span two additional disk levels (not shown). In some embodiments, one or more new pedicle screws 510 may be placed, and a second rod extension 350 of variable length chosen to span the newly placed pedicle screws 510.

In assembly, operation and use, a spinal implant system, similar to the systems and methods described herein, can be employed with a surgical procedure, such as, for example, a surgical treatment of an applicable condition or injury of an affected section of a spinal column and adjacent areas within a body. In some embodiments, the spinal implant system includes a spinal construct, similar to those described herein, which can be employed in a surgical treatment such as an index surgery and/or a revision surgery to revise, repair and/or extend an existing spinal construct. In some embodiments, the spinal implant system includes components employed in a revision surgery to connect with an existing spinal construct and extend the existing spinal construct to span one or more spinal levels. In some embodiments, the existing spinal construct may include one or more implants connected or fixed with tissue in a prior or different surgical procedure, separate in time and/or over a duration of time in the same surgical procedure. In some embodiments, during a surgical treatment, components of the spinal implant system may be completely or partially revised, removed or replaced.

Figure 8:
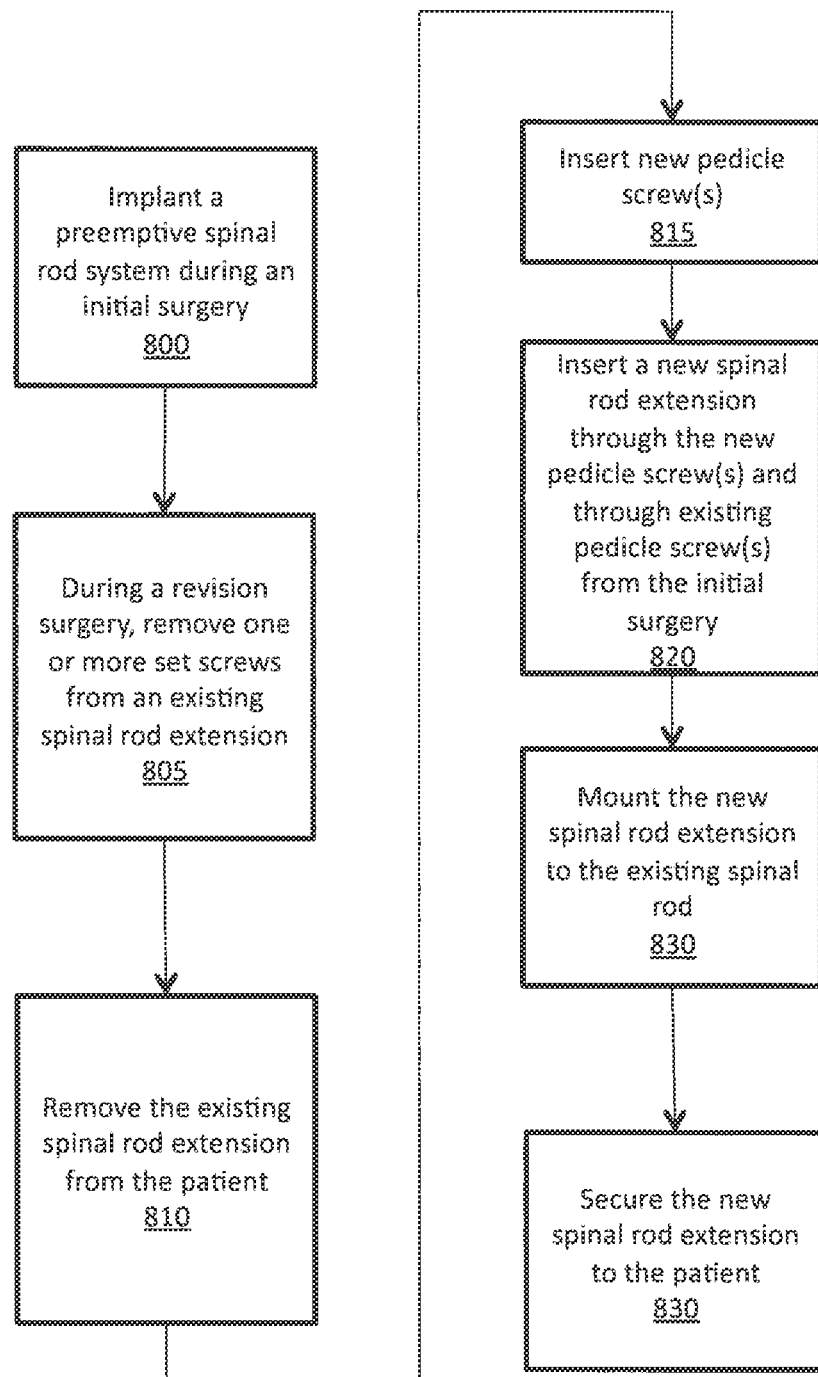
FIG. 8 is a flow diagram of the steps of a method of one embodiment of a system in accordance with the principles of the present disclosure.

For example, as shown in FIG. 8, the components of a spinal implant system, as described herein, can be employed with a method for treating a spine using a preemptive spinal rod system. In some embodiments, fewer, additional, and/or different operations may be performed, in some embodiments, an operation 800 includes implanting a preemptive spinal rod system during an initial or index surgery on a patient. The preemptive spinal rod system includes a spinal rod with one or more spinal rod extensions mounted thereto, as described herein. In some embodiments, the spinal rod can include a spinal rod extension mounted to each end of the spinal rod. In some embodiments, more than one spinal rod extension may be mounted to each end of the spinal rod. In some embodiments, the preemptive spinal rod system can be pre-formed to the patient's anatomy and/or cut to length in advance of or during surgery.

In some embodiments, during surgery, a surgeon makes an incision during open procedures or a series of incisions during minimally invasive percutaneous procedures such that a number of pedicle screws can be secured to the patient. The preemptive spinal rod system is then inserted through U-shaped heads of pedicle screws. In some embodiments, the pedicle screw extensions are removed in cases when percutaneous screws are placed. Set screws are inserted into the U-shaped heads to keep the preemptive spinal rod system within the U-shaped pedicle screw heads, as described herein, and the incision(s) closed. The rods and rod extensions of the preemptive spinal rod system are inserted and positioned with the patient, as described herein, with surgical instruments. In some embodiments, an insertion tool may be detachably mounted to ends of rods and rod extensions of the preemptive spinal rod system. In connection with a surgical procedure, to treat a selected section of vertebrae, a surgeon obtains access to a surgical site including vertebrae in any appropriate manner, such as through incision and retraction of tissues. In some embodiments, the spinal implant system can be used in any surgical method or technique including open surgery, mini-open surgery, minimally invasive surgery and percutaneous surgical implantation, whereby vertebrae is accessed through a mini-incision, or a sleeve that provides a protected passageway to the area. Once access to the surgical site is obtained, the particular surgical procedure can be performed for treating the spine disorder.

In some cases, a patient who has had an initial or index spinal surgery may experience issues with spinal segments that are adjacent to the spinal segments secured by an initial implant. In some cases, the patient needs a revision surgery to correct any issues. In an operation 805, during such a revision surgery, the surgeon removes one or more set screws that maintain an existing spinal rod extension, for example, inserted during the initial surgery as part of the preemptive spinal rod system, within the U-shaped heads of pedicle screws. In an operation 810, the surgeon removes the existing spinal rod extension from the patient using an insertion/removal tool or tools, as described herein. Removal of the existing spinal rod extension includes disconnecting the extension from the existing spinal rod of the preemptive spinal rod system by removing/loosening the screw(s) or other fastener(s) that are used to secure the connection, as described herein.

In an operation 815, the surgeon inserts one or more new pedicle screws into the patient that will be used to secure a new spinal rod extension, as described herein. The new (or replacement) spinal rod extension, which can be of a different length and/or shape than the existing spinal rod extension, is used to correct the issue, which prompted the revision surgery. In an operation 820, the surgeon inserts the new spinal rod extension through the newly inserted pedicle screw heads and also through one or more existing pedicle screw heads that are part of the pedicle screw(s) used to secure the removed spinal rod extension from the initial surgery. In some embodiments, the existing pedicle screw(s) may be removed or repositioned. The new spinal rod extension can be inserted using an insertion tool, which is detachably secured to an end of the new spinal rod extension.

In an operation 825, the surgeon mounts the new spinal rod extension to the existing spinal rod that was inserted during the initial surgery, as described herein. The surgeon mounts the new extension to the existing spinal rod using one or more screw(s) or other fastener(s), as described herein. In an operation 830, the surgeon secures the new spinal rod extension to the patient by inserting set screws into the U-shaped heads of all pedicle screws through which the new spinal rod extension travels or extends.

In some embodiments, the components of the preemptive spinal rod systems described herein can include rods, extensions and portions thereof having a linear, axial and/or straight configuration that can be placed as-is into a patient. In some embodiments, the components of the preemptive spinal rod systems described herein can include rods, extensions and portions thereof being flexible and bendable prior to implantation to match the patient's anatomy. In some embodiments, the components of the preemptive spinal rod systems described herein can include rods, extensions and portions thereof having a pre-contoured configuration, for example, pre-bent to match a patient's lordotic or kyphotic spine segment.

Upon completion of the procedure, the surgical instruments, assemblies and non-implanted components of the spinal implant system are removed from the surgical site and the incision is closed. One or more of the components of the spinal implant system can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of the spinal implant system.

In some embodiments, the spinal implant system includes an agent, which may be disposed, packed, coated or layered within, on or about the components and/or surfaces of the spinal implant system. In some embodiments, the agent may include bone growth promoting material, such as, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration. In some embodiments, the existing fastener implant or pedicle screw, as described herein, may include sagittal angulation screws, mono-axial screws, uni-planar screws, fixed screws, anchors, hooks, tissue penetrating screws, conventional screws, expanding screws, wedges, anchors, buttons, clips, snaps, friction fittings, compressive fittings, expanding rivets, staples, nails, adhesives, posts, connectors, fixation plates and/or posts. In some embodiments, the spinal implant system can include one or a plurality of spinal constructs, rods and/or extensions, such as those described herein, which may be employed with a single vertebral level or a plurality of vertebral levels. In some embodiments, the spinal implant system can include one or a plurality of spinal constructs, rods and/or extensions, such as those described herein, may be engaged with vertebrae in various orientations, such as, for example, series, parallel, offset, staggered and/or alternate vertebral levels.

It will be understood that various modifications may be made to the embodiments disclosed herein. Therefore, the above description should not be construed as limiting, but merely as exemplification of the various embodiments.

Those skilled in the art will envision other modifications within the scope and spirit of the claims appended hereto.

What is claimed is:

1. A preemptive spinal rod system comprising:
a rod portion extending between opposite first and second end surfaces, the rod portion including an outer surface extending from the first end surface to the second end surface, the rod portion defining a rod dimension;
a male mating part extending outwardly from the first end surface and the outer surface;
a rod extension portion including a shaft and a connector, the connector being monolithically formed with the shaft, the connector having a maximum width, the maximum width of the connector being greater than a maximum width of the male mating part, the connector comprising a female mating part defining a cavity configured for disposal the male mating part to form a connection having a dimension the same as the rod dimension, the shaft defining a diameter dimension the same as the rod dimension; and
a fastener configured to extend through the connector such that an end of the fastener directly engages the male mating part within the cavity to secure the rod extension portion to the rod portion.

2. A spinal construct as recited in claim 1, wherein the cavity has a non-circular shape matching a shape of the male mating part.

3. A spinal construct comprising:
an existing spinal rod implant extending between opposite first and second end surfaces, the existing spinal rod implant including an outer surface extending from the first end surface to the second end surface, the existing spinal rod implant defining a rod dimension;
a male mating part extending outwardly from the first end surface and the outer surface;
at least one extension including a shaft and a connector, the connector being monolithically formed with the shaft, the connector comprising a mating surface defining a female mating part configured for disposal of the male mating part to form a connection having a dimension the same as the rod dimension, the shaft defining a diameter dimension the same as the rod dimension, the connector having a maximum width, the maximum width of the connector being greater than a maximum width of the male mating part; and
a setscrew configured to extend through the connector such that an end of the setscrew directly engages the male mating part within the connector to fix the existing spinal rod implant with the at least one extension.

4. A spinal construct as recited in claim 3, wherein the existing spinal rod implant includes a shaft, the shaft of the existing spinal rod defining the rod dimension, the shaft of the existing spinal rod implant including the end surfaces and the outer surface.

5. A spinal construct as recited in claim 3, wherein the existing spinal rod implant includes a shaft having a constant rod diameter dimension, the shaft of the existing spinal rod implant including the end surfaces and the outer surface.

6. A spinal construct as recited in claim 3, wherein the existing spinal rod implant includes a shaft, the shaft of the existing spinal rod defining the rod dimension, the shaft of the existing spinal rod including the end surfaces and the outer surface, the male mating part including a first mating surface extending outwardly from the first end surface and a second mating surface extending outwardly from the outer surface.

7. A spinal construct as recited in claim 3, wherein the existing spinal rod implant includes a shaft having a constant rod diameter dimension, the shaft of the existing spinal rod including the end surfaces and the outer surface, the male mating part including a first portion extending outwardly from the first end surface and a second portion extending outwardly from the outer surface.

8. A spinal construct as recited in claim 3, wherein the at least one extension comprises a plurality of extensions.

9. A spinal construct as recited in claim 3, wherein the shaft defines a second rod dimension, the second rod dimension being the same as the dimension of the connection.

10. A spinal construct as recited in claim 3, wherein the shaft defines a second rod dimension, the second rod dimension being the same as the dimension of the connection, the mating surface of the at least one extension being a female mating part.

11. A spinal construct as recited in claim 3, wherein the male mating part is a first mating part extending outwardly from the first end surface, the first male mating part being engageable with a first rod extension, the spinal construct including a second male mating part extending from the second end surface, the second male mating part being engageable with a second rod extension.

12. A spinal construct as recited in claim 3, wherein the at least one extension comprises a first rod extension and a second rod extension, the male mating part being a first male mating part extending outwardly from the first end surface, the first male mating part being engageable with a female mating part of the first rod extension, the spinal construct including a second male mating part extending outwardly from the second end surface and the outer surface, the second male mating part being engageable with a female mating part of the second rod extension.

13. A spinal construct as recited in claim 3, wherein the dimension of the connection includes a medial-to-lateral width.

14. A spinal construct as recited in claim 3, wherein the end of the setscrew presses against an outer surface of the male mating part.

15. A spinal construct as recited in claim 3, wherein the connection is disposable within a cavity of a receiver of an existing pedicle screw implant.

16. A spinal implant system comprising:
an existing spinal rod implant extending between opposite first and second end surfaces, the existing spinal rod implant including an outer surface extending from the first end surface to the second end surface, the existing spinal rod implant defining a rod dimension;
a male mating part extending outwardly from the first end surface and the outer surface:
at least one existing fastener implant, each of the existing fastener implants defining a cavity configured for disposal of the existing spinal rod implant;
a first, removable extension including a shaft and a connector, the connector being monolithically formed with the shaft, the connector comprising a mating surface defining a female mating part configured for disposal of the male mating part to form a connection having a dimension the same as the rod dimension, the shaft defining a diameter dimension the same as the rod dimension, the connector having a maximum width, the maximum width of the connector being greater than a maximum width of the male mating part;
a setscrew configured to extend through the connector such that an end of the setscrew directly engages the male mating part within the connector to fix the existing spinal rod implant with the first extension; and a second extension configured to replace the first extension, the second extension including a shaft and a connector, the connector of the second extension being coupled to the shaft of the second extension, the connector of the second extension comprising a mating surface configured for disposal of the male mating part to form a connection having a dimension the same as the rod dimension, the connector of the second extension having a maximum width, the maximum width of the connector of the second extension being greater than a maximum width of the shaft of the second extension.

17. A spinal implant system as recited in claim 16, wherein the existing spinal rod implant includes a shaft having a constant rod diameter dimension, the shaft including the end surfaces and the outer surface.

18. A spinal construct as recited in claim 16, wherein the dimension of the connection includes a medial-to-lateral width.

* * * * *